United States Patent [19]

Diamond

[11] Patent Number: 6,086,372

[45] Date of Patent: Jul. 11, 2000

[54] DENTAL AND ORAL PREPARATION

[75] Inventor: Jeffrey H. Diamond, Palm Beach, Fla.

[73] Assignee: Block Drug Company, Inc., Jersey City, N.J.

[21] Appl. No.: 08/868,999

[22] Filed: Jun. 4, 1997

[51] Int. Cl.[7] ..................................................... A61K 7/16
[52] U.S. Cl. .............................. 433/216; 424/48; 424/59; 433/215; 433/216
[58] Field of Search ........................ 424/48–59; 433/215, 433/216

[56] References Cited

U.S. PATENT DOCUMENTS

| | | |
|---|---|---|
| Re. 32,771 | 10/1988 | Eoga . |
| 1,526,940 | 2/1925 | Staegemann . |
| 2,124,971 | 7/1938 | Eisenberg et al. . |
| 2,519,665 | 8/1950 | Klippert . |
| 2,744,049 | 5/1956 | Salzmann et al. . |
| 2,921,886 | 1/1960 | Panepinto . |
| 3,137,632 | 6/1964 | Shiraldi . |
| 3,164,524 | 1/1965 | Fand et al. . |
| 3,497,590 | 2/1970 | Elgen . |
| 3,553,314 | 1/1971 | Francis . |
| 3,553,315 | 1/1971 | Francis . |
| 3,652,420 | 3/1972 | Hill . |
| 3,737,522 | 6/1973 | Francis . |
| 3,839,213 | 10/1974 | Hill . |
| 3,840,657 | 10/1974 | Norfleet . |
| 3,899,437 | 8/1975 | Regan et al. . |
| 3,935,304 | 1/1976 | Januszewski et al. . |
| 3,935,305 | 1/1976 | Delaney et al. . |
| 3,937,804 | 2/1976 | Delaney et al. . |
| 3,947,570 | 3/1976 | Pensak et al. . |
| 3,966,901 | 6/1976 | Cullum et al. . |
| 3,988,434 | 10/1976 | Schole et al. . |
| 3,992,519 | 11/1976 | Hofmann et al. . |
| 4,115,293 | 9/1978 | Schoenholz et al. . |
| 4,130,636 | 12/1978 | Tomlinson . |
| 4,150,151 | 4/1979 | Pader et al. . |
| 4,155,868 | 5/1979 | Kaplan et al. . |
| 4,206,198 | 6/1980 | Schmolka . |
| 4,223,003 | 9/1980 | Scheller . |
| 4,303,648 | 12/1981 | Witzel et al. . |
| 4,314,990 | 2/1982 | Denny, Jr. et al. . |
| 4,323,552 | 4/1982 | Schmolka . |
| 4,383,987 | 5/1983 | Kiozpeoplou . |
| 4,393,042 | 7/1983 | Battista . |
| 4,409,202 | 10/1983 | Witzel et al. . |
| 4,420,471 | 12/1983 | Elton et al. . |
| 4,428,929 | 1/1984 | Wicheta et al. . |
| 4,431,631 | 2/1984 | Clipper et al. . |
| 4,511,486 | 4/1985 | Shah . |
| 4,518,520 | 5/1985 | Eoga . |
| 4,522,806 | 6/1985 | Muhlemann et al. . |
| 4,537,778 | 8/1985 | Clipper et al. . |
| 4,540,504 | 9/1985 | Eoga . |
| 4,545,979 | 10/1985 | Ambike et al. . |
| 4,550,018 | 10/1985 | Ambike et al. . |
| 4,610,872 | 9/1986 | Lynch . |
| 4,657,758 | 4/1987 | Goldemberg et al. . |
| 4,666,708 | 5/1987 | Goldemberg et al. . |
| 4,684,517 | 8/1987 | Clipper et al. . |
| 4,701,223 | 10/1987 | Eoga . |
| 4,747,417 | 5/1988 | Beskin . |
| 4,807,649 | 2/1989 | Eoga . |
| 4,992,259 | 2/1991 | Schiraldi et al. . |
| 5,032,385 | 7/1991 | Reed et al. . |
| 5,130,122 | 7/1992 | Tabibi et al. . |
| 5,145,664 | 9/1992 | Thompson . |
| 5,178,869 | 1/1993 | Ebine et al. . |
| 5,514,366 | 5/1996 | Diamond . |
| 5,662,888 | 9/1997 | Diamond . |

*Primary Examiner*—Nicholas D. Lucchesi

[57] ABSTRACT

An oral preparation for removing deposits on surfaces in the oral cavity in conjunction with a toothbrush. The preparation includes at least one nonionic surfactant in a concentration range of from about 1.0% to about 40.0% by weight and at least one essential oil in a concentration range of from about 0.2% to about 13.0% by weight.

20 Claims, No Drawings

DENTAL AND ORAL PREPARATION

FIELD OF THE INVENTION

The invention relates to dental and oral hygiene, and in particular, to a preparation to solubilize, dissolve, disperse, detach, and/or otherwise remove deposits from the teeth, gums, tongue, and other surfaces in the oral cavity in conjunction with a toothbrush.

BACKGROUND OF THE INVENTION

It is well known that tobacco use, whether in the form of chewing, smoking, or otherwise, can cause the deposition of materials on the teeth, tongue, gums, and other surfaces in the oral cavity of tobacco users. The result of the deposition of these materials is well known by any one who uses tobacco or knows someone who uses tobacco. The most well known of these effects include the discoloration of the teeth and other surfaces within the oral cavity such as the gums and tongue and the causing of bad breath. Tobacco stained teeth can be unsightly and bad breath can be unpleasant for the tobacco users and those he or she comes into contact with. Additionally, as described below, the materials deposited on the interior surface of the mouths of tobacco users can lead to health problems, such as tooth decay and gum disease. It is also well known that food, drink, other materials that pass through or enter the oral cavity and their constituents can be deposited on the surfaces of peoples' oral cavities.

The major constituent of deposits caused by tobacco users is commonly known as "tar". Tobacco tar is loosely defined as a dark, oily, viscid blend of polycyclic aromatic and aliphatic hydrocarbons, although tar also contains other compounds. Tar may also be defined as a product resulting from the destructive distillation of tobacco.

Tar is produced as tobacco in a cigarette, cigar, or pipe burns and as tobacco is chewed. The tar is contained within the smoke produced by the burning of the tobacco. Other materials in tobacco smoke or in chewed tobacco may also stain the teeth.

As a smoker smokes a cigarette, pipe, or cigar, he or she inhales the tar along with the other tobacco combustion products as the smoke is sucked into the mouth and eventually into the lungs. The smoke is then blown out of the body as the smoker exhales, passing through the mouth of the smoker once again. Therefore, the smoke passes through the mouth of the smoker twice, upon inhalation and exhalation, providing ample opportunity for the compounds in the tar to come into contact with the teeth, gums, tongue, and other surfaces in the oral cavity and be deposited thereon. Obviously, the more a person smokes, the more tar will be deposited in the mouth of the smoker.

As chewers of tobacco chew the tobacco and materials contained within the tobacco will form a solution with saliva, enzymes in saliva will also breakdown the tobacco. The tobacco and saliva solution contain tar along with the other tobacco products. The tobacco and saliva solution and materials contained in both can be deposited on the surfaces within the oral cavities of the chewers as they chew. Obviously, the more a person chews tobacco, the more tar and other materials will be deposited in the oral cavities of tobacco chewers.

Dentists and hygienists can immediately detect tobacco users by the heavy staining of the lingual surface of the mandibular anterior teeth. These stains are observed as being resinous in nature. According to a study by the Centers for Disease Control, smokers' teeth are generally twice as stained as non-smokers'. McKendrick, Barbenel, and McHugh, Indiana School of Dentistry (1970).

Due to the hydrophobic nature of the compounds contained within the tar, the tar is not easily dissolved, solubilized, detached, and/or dispersed by commonly available over the counter mouth treatments such as toothpastes and gels. As a result, tobacco tar can build up on the teeth, dentures, denture plates, artificial teeth and other surfaces of tobacco users' oral cavities, causing, among other things, staining of plaque and calculus and an aesthetically displeasing appearance of the tobacco users' teeth, gums, and other surfaces in their mouths. Additionally, since the compounds in tar have an unpleasant aroma, their deposition and residence within the mouth of tobacco users can cause chronic halitosis.

The difficulty in removing tar and other deposits resulting from tobacco use within the oral cavities of tobacco users is increased by there viscid nature. Many compounds contained within food, drink, other materials that pass through or enter peoples' oral cavities and their constituents can also be deposited on surfaces of peoples' oral cavities.

Therefore, as tobacco tar and other deposits build up on surfaces in peoples' mouths, the surfaces are discolored. Also, the breath of tobacco users takes on a malodorous nature. In fact, tar and other tobacco materials can become incorporated into plaque and calculus that form on teeth. Because of its especially tenacious nature, the calculus is only removable by a dentist or dental hygienist with a steel pick.

Because tobacco tar can reduce immune response, bacteria has the opportunity to proliferate. Bacterial can cause tooth decay, gingivitis, bleeding and swelling of the gums, and periodontal disease. Therefore, tobacco tar is a real health problem.

As discussed above, tobacco tar is especially difficult to remove once deposited on the surface of the teeth, gums, tongue, and the rest of the oral cavity. Materials in food and other substances coming into contact with peoples' mouths can also be just as difficult to remove. In an attempt to remove tar and other deposits from teeth, products such as toothpastes and gels were developed that claim to remove tobacco tar as well as various other stains, such as blueberry and wine.

Known products that claim to remove tobacco stains or deposits on teeth have a minimal effect primarily through physical abrasion. Such products act in a manner similar to how sandpaper removes the surface layer of paint from wood, for example. These products typically include an aluminum or silicon based abrading material to physically remove the tar from the surfaces in the mouth.

Prior to the invention by the present inventor of the composition disclosed in U.S. Pat. No. 5,514,366 to the same inventor as the present invention, the entire disclosure of which is hereby incorporated by reference, and marketed under the tradename "TARGON", all known anti-tobacco stain products on the market are in toothpaste form. These known products do not include ingredients which dissolve, solubilize, detach and/or disperse tobacco stains or tar, but rather, remove tobacco stains or tar primarily through physical abrading action. In other words, they rub the tar off the surfaces of the mouth as the smoker brushes his or her teeth. Known toothpastes that claim to remove tobacco stains or tar are some of the most abrasive toothpastes on the market.

Unfortunately, the abrading materials in these known toothpastes do not differentiate between tobacco tar and other materials, such as the actual surface of the teeth. Therefore, in addition to removing tobacco tar, these materials can actually remove enamel from the teeth themselves. Removal of the enamel could cause the teeth to become sensitive, which can cause individuals to avoid brushing their teeth, which may lead to tooth loss.

For example, the outer enamel layer can be partially removed by these known products, thereby damaging the teeth and creating scratches on the surface of the teeth. These scratches can make the teeth more susceptible to decay and endanger the softer interior layers of the teeth. This is why toothpastes for sensitive teeth are very low in abrasiveness. Also, scratches on teeth can increase the surface area of the teeth, thereby increasing the number of places where bacteria can attach to the surface of the tooth and potentially cause tooth decay.

These abrasive cleaners are also not capable of removing tar from microscopic concavities in the teeth which are too small for the abrasives to enter or from any surface which the abrasive materials can not be rubbed against, such as the interproximal spaces between teeth and some gingival spaces between the teeth and gums. Therefore, these known abrasive materials that claim to remove tobacco tar from the surfaces of teeth can in fact leave much tar untouched on teeth and oral soft tissue and actually cause damage to the oral cavity. For these reasons, dentists usually do not recommend the use of these known abrasive toothpastes.

SUMMARY OF THE INVENTION

The inventor of the present invention realized that as opposed to abrading compositions, it would be desirable to have a toothpaste that could remove tar from all surfaces in the mouth of a smoker and not physically harm the tooth surface. The inventor also realized that it would be advantageous to have a toothpaste that could dissolve, solubilize, detach and/or disperse the tobacco tar, thereby reducing the need for abrasiveness as the primary means for removing the tobacco tar from the mouth without adverse effects, as described above. However, no known available toothpaste product, whether or not available on the market today, is directed to or is capable of performing the function of dissolving or dispersing tobacco tar effectively.

The present invention unexpectedly removes tobacco tar by dissolving the tobacco tar with minimal abrasive action and without physically damaging teeth.

In view of the above, it is an object and an advantage of the present invention to provide a toothpaste that removes tobacco tar without resorting primarily to the use of abrading compositions.

Accordingly, it is an object and advantage of the present invention to provide a toothpaste that removes tar from teeth in the mouth of a smoker without physically harming the tooth surface.

An additional object and advantage of the present invention are to provide a toothpaste that dissolves, solubilizes, detaches, and/or disperses tobacco tar, thereby reducing the need for abrasiveness as the primary means for removing the tobacco tar and/or stains from surface in the oral cavities of tobacco users.

In accordance with these and other objects and advantages, preferred aspects of the present invention provide an oral preparation for removing deposits on surfaces in the oral cavity in conjunction with a toothbrush. The preparation includes at least one nonionic surfactant in a concentration range of from about 1.0% to about 40.0% by weight and at least one essential oil in a concentration range of from about 0.2% to about 13.0% by weight.

According to other preferred aspects, the present invention provides a method for removing deposits on surfaces of teeth, dentures, dental plates, and gums and surfaces in the oral cavity. The method includes introducing into the oral cavity an oral preparation including at least one nonionic surfactant in a concentration range of from about 1.0% to about 40.0% by weight and at least one essential oil in a concentration range of from about 0.2% to about 13.0% by weight. Then, surfaces in the oral cavity are brushed with a toothbrush.

Additionally, preferred aspects of the present invention provide a method for removing deposits on surfaces in the oral cavity resulting from the introduction into the oral cavity tobacco or material created by the burning of tobacco. The method includes introducing into the oral cavity an oral preparation including at least one nonionic surfactant in a concentration range of from about 1.0% to about 40.0% by weight and at least one essential oil in a concentration range of from about 0.2% to about 13.0% by weight. Surfaces in the oral cavity are then brushed with a toothbrush.

Still other objects and advantages of the present invention will become readily apparent to those skilled in the art from the following description. The detailed description shows and describes on preferred embodiments of the present invention so as to illustrate the best mode contemplated for carrying out the invention. As those skilled in art will realize, the present invention includes other and different embodiments. Details of the present invention may be modified in various respects, without departing from the present invention. Accordingly, the description contained herein should be regarded as illustrative in nature rather than restrictive.

DETAILED DESCRIPTION OF THE PREFERRED EMBODIMENTS

The active ingredients of the oral preparation of the present invention for removing deposits on the teeth, gums, tongue, and other surfaces in the oral cavity preferably include at least one nonionic surfactant and at least one essential oil. The essential oil may be cyclic. For example, the essential oil may be aromatic. The present invention may also include at least one anionic surfactant, although the present invention will still function well without an anionic surfactant component. Additionally, the preparation of the present invention may also include flavorings, a vehicle for the preparation, humectants, abrasives, fluoride, antioxidants, coloring, preservatives, at least one viscosity increasing material, and/or other therapeutic agents.

It has been found that including the ingredients in the combination and amounts according to the present invention provides the preparation of the present invention with the ability to dissolve, solubilize, detach and/or disperse material deposited on the surface of the teeth, gums, tongue, and other surfaces of the oral cavity. Specifically, the present invention has the ability to dissolve, solubilize, detach and/or disperse tobacco tar on contact, permitting more tar to be brushed away by a toothbrush. Such an ability to dissolve, solubilize, detach and/or disperse tar is unknown among known toothpastes. The preparation of the present invention may be included in toothpastes or gels, or powders, or in any other effective form, simply with the combination of the above ingredients.

The nonionic surfactant component of the present invention may act as a tar solubilizer and to a lesser extent a flavor solubilizer, among other things. Any pharmaceutically or orally acceptable nonionic surfactant may be used according to the present invention. Examples of nonionic surfactants which may be used in the present invention include glycerol-polyethylene glycol oxystearate (PEG 40, PEG 60, Cremophor RH40 and 60, respectively, available from BASF), polyoxyethylene esters or sorbitol laurate esters, such as polyoxyethylene sorbitan monolaurate, polyoxyethylene sorbitan monoisostearate, polyoxyethylene sorbitan monostearate, polyoxyethylene sorbitan monooleate, polyoxyethylene or sorbitol laurate esters including polysorbates, and block polymers of polyoxyethylene and polyoxypropylene (pluronic 127). The concentration range of nonionic surfactants included in the present invention may be from about 1.0% to about 40.0% by weight. Alternatively, the concentration range of nonionic surfactants included in the present invention may be from about 6.5% to about 40.0% by weight. Nonionic surfactants preferably are present in an amount sufficient to contribute to the tar solubilizing and removing function of the present invention.

Mouthwash typically includes nonionic surfactants to disperse flavor oils in aqueous media and to create low foaming properties, for example. Alternatively, nonionic surfactants may also be used in the prior art only to stabilize certain ingredients. Toothpastes rarely, if ever, include nonionic surfactants. If toothpastes include nonionic surfactants, the nonionic surfactants typically function to solubilize and/or stabilize active ingredients.

On the other hand, the present invention includes nonionic surfactants for the purpose of co-solubilizing, dispersing, and/or dissolving the tobacco tar. The concentration ranges of nonionic surfactants in the present invention helps the nonionic surfactants to preform this function. The most common types of nonionic surfactants are polyoxyethylene derivatives of sorbitan fatty acid esters and polyoxyethylene-polyoxypropylene block copolymers. Although the potential number of surfactants represented by these chemical classes is unlimited, only a few specific compounds are commercially available in the purity adequate for use in oral hygiene products. However, one skilled in the art would recognize that nonionic surfactants available in the future could also be used.

Polyoxyethylene derivatives of sorbitan fatty acid esters are, for the most part, hydrophilic, with varying solubility in water and organic solvents, depending upon their structure. They are prepared by the ethoxylation of 1,4-sorbitan mono- or polyesters, yielding a structure with an oxygen bridge on carbons 1 and 4 and a fatty acid moiety at the other end of the molecule. The polyoxyethylene sorbitan fatty acid esters are excellent oil and/or water phase emulsifiers and are typically used for the dispersion or solubilization of flavor in aqueous media.

The present invention employs nonionic surfactants to solubilize, dissolve, detach and/or disperse tobacco tar on a smokers teeth and gums. Long commercial use has led some to designate polyoxyethylene sorbitan fatty acids as Tweens, sorbitan esters as Spans, and polyoxyethylene fatty acid esters as Brijs. Other, related commercial derivatives are frequently referred to as Myrjis and Arlacels.

Another class of nonionic surfactants includes polyoxyethylene-polyoxypropylene block copolymers. These compounds are represented by the formula $HO(CH_2CH_2O)_x(CHMeCH_2O)_y(CH_2CH_2O)_xH$. Commercial products including these compounds include mixtures of the copolymers, as expected from the complexity of the polymerization. These products are commercially available as Pluronics. Typically, these products are utilized to dissolve flavor ingredients in aqueous media. As noted above, in the present invention, these materials are used to dissolve, solubilize, detach and/or disperse tobacco tar on a smokers teeth, gums, and or other oral cavity surfaces.

A preferred embodiment of the present invention utilizes PEG 40 hydrogenated castor oil, Cremophor RH40, available from BASF, as the nonionic surfactant. This is because this nonionic surfactant is highly effective in dissolving tobacco tar and has very little aftertaste.

The present invention may also include at least one anionic surfactant. The anionic surfactant component of the present invention may act as a sudsing agent and tar co-solubilizer, and/or dispersion aid, among other things. Anionic surfactants may also contribute therapeutically, in addition to enhancing enjoyment of dentifrices because of their foaming properties. Any pharmaceutically or orally acceptable anionic surfactant may be used according to the present invention.

An example of an anionic surfactant that may be used in the present invention include sodium lauryl sulfate. Sodium lauryl sulfate is an anionic surfactant that is typically used in toothpastes and dentifrices. It is a long chain fatty alcohol sulfate with a molecular formula of $RSO_3Na$, where R represents a mixture of long chain saturated alkyl chains. Other commonly known and utilized anionic surfactants include sodium cocomonoglyceride sulfonate and alpha-olefin sulfonates.

The concentration range of anionic surfactants included in the present invention is from about 0.1% to about 3.5% by weight. Alternatively, the present invention may include anionic surfactants in a concentration range of from about 0.3% to about 2.5%, by weight. Preferably, the anionic surfactants are included in the present invention in a concentration range of no more than about 1.5% by weight to reduce foaming for commercial acceptance.

In contrast to the prior art in which anionic surfactants are included in toothpastes to create mild sudsing and to help remove some oral debris such as food and related oils, the present invention may include anionic surfactants in concentration ranges high enough in conjunction with other ingredients to actually dissolve, solubilize, detach and/or disperse the tobacco tar on teeth, gums, and/or other surfaces within the oral cavity.

In contrast to anionic surfactants, cationic surfactants with recognized potential for therapeutic benefits do not foam well enough to provide an amount of foam typically desired by consumers.

Tobacco tar contains much higher molecular weight materials than the standard essential oils used as flavors and other therapeutic agents. Therefore, to solubilize tobacco tar, the amount of nonionic surfactants, essential oils, and optionally, anionic surfactants, if anionic surfactants are included in the formulation, as a percentage of total weight is much greater in the present invention than in the prior art. In fact, toothpaste formulations typically do not include any nonionic surfactants.

It is the high concentration and combination of surfactants in the present invention that, at least in part, provides the present invention with its superior and unexpected ability to dissolve, solubilize, detach and/or disperse tobacco tar as compared prior art toothpastes. Most prior art toothpastes contain from about 0.02% to about 2.0% by weight surfactants. On the other hand, the present invention includes total surfactants in a concentration range of from about 1.0% to about 43.5% by weight.

The present invention also preferably includes a different surfactant blend than prior art toothpastes. The only oils that prior art toothpastes are designed to solubilize and/or disperse are the essential oils' flavor, not the oils included in tobacco tar and other oily substances deposited in the mouth. Preferably, the present invention includes a combination of anionic and nonionic surfactants, including at least one nonionic and optionally at least one anionic.

The active ingredients of the present invention also include at least one essential oil. The essential oil may be cyclic. For example, the essential oil may be aromatic.

The essential oil component of the present invention may act as a tar solubilizer, dissolver, detacher, and/or dispersant, among other things. Any pharmaceutically or orally acceptable essential oil may be used according to the present invention. Examples of essential oils that the present invention may include are methyl salicylate, anise, anethol, bergamot, camphor, cinnaminic anhydrides, clove, eucalyptol, peppermint, spearmint, and thyme, among others.

The concentration range of the at least one essential oil included in the present invention is from about 0.2% to about 13.0% by weight. Alternatively, at least one essential oil may be included in the present invention in a concentration range of from about 0.2% to about 7.5% by weight. Additionally, at least one essential oil may be present in a composition according to the present invention in a concentration range of from about 2.0% to about 13.0% by weight. Furthermore, at least one essential oil may be present in a concentration range of from about 2.0% to about 7.5% by weight. Other concentration ranges include from about 0.2% to about 5.5%, about 2.0% to about 5.5%, about 5.5% to about 7.5%, about 5.5% to about 13.0%, 0.5% to about 5.5%, about 0.5% to about 7.5%, about 0.5% to about 13.0%, at least about 0.2%, at leat about 0.5%, at least about 5.5%, and at least about 7.5%, all by weight. Essential oils preferably are present in an amount sufficient to contribute to the tar solubilizing and removing function of the present invention.

In the prior art, essential oils are used mainly as flavors and are typically used in a concentration range of from only about 0.05% to about 0.30% by weight for flavoring. Typically, essential oils are not utilized for other functions. In fact, essential oils are typically not present in sufficient concentration to function other than to provide a slight antimicrobial effect and as a flavoring.

On the other hand, according to the present invention, essential oils in combination with the nonionic surfactants and optionally anionic surfactants are present in concentrations higher than known in the art. At these concentrations, the essential oils, nonionic surfactants and optionally anionic surfactants help to dissolve, solubilize, detach and/or disperse significantly more tobacco tar than known dental preparations.

On the other hand, the present invention includes essential oils in combination with the nonionic and optionally anionic surfactants also present in higher concentrations than are known in the prior art help to dissolve, solubilize, detach and/or disperse significantly more tar than known prior art dental preparations.

Preferred embodiments of the present invention include methyl salicylate as the essential oil. Methyl salicylate, as one of the essential oils discussed above, may act as a tobacco tar solubilizer, dissolver, detacher and/or dispersant. Of course, the composition may include other essential oils in addition to or in place of methyl salicylate.

The present invention may include methyl salicylate in a concentration range of from about 0.2% to about 13.0% by weight. Alternatively, the present invention may include methyl salicylate in one of the concentration ranges discussed above for the at least one essential oil. Methyl salicylate preferably is present in an amount sufficient to contribute to the tar solubilizing and removing function of the present invention.

Methyl salicylate is typically manufactured synthetically with the molecular formula $O-HOC_6H_4CO_2CH_3$. Methyl salicylate acts as an antimicrobial agent and a flavor. However, most importantly, in the concentration ranges of the present invention, methyl salicylate solubilizes, dissolves, detaches and/or disperses tobacco tar from surfaces within the oral cavities of smokers.

A significant difference between the present invention and the prior art is that the prior art utilizes methyl salicylate primarily as a flavoring. On the other hand, embodiment of the present invention that include methyl salicylate preferably include it in a concentration range that will solubilize, dissolve, detach and/or disperse tobacco tar in conjunction with other ingredients.

The present invention may include only at least one nonionic surfactant and at least one essential oil. Adding at least one vehicle or backbone and/or other ingredient may make the composition more commercially successful, but such is not necessary to make the present invention function to remove, disperse, solubilize, detach and/or dissolve tobacco tar.

As stated above, the present invention may include a vehicle or backbone for the oral preparation, which may include humectants. Additionally, the present invention may include binders or thickeners, sweeteners, flavors, coloring, and preservatives.

The preferred vehicle for a preparation according to the present invention is glycerin. Other examples of vehicles are water and sorbitol. With glycerin used as the vehicle or backbone to prepare such a composition, the glycerin is present in a concentration range of from about 5.0% to about 40.0% by weight. Additional vehicles or backbones that may be included in preparations according to the present invention include pastes, gels, and other humectants.

The most common humectants are glycerin and sorbitol. However, any pharmaceutically or orally acceptable humectant may be used in the preparations of the present invention. The roles of humectants include providing a vehicle for abrasives, surfactants, active ingredients, and any other components that the composition of the present invention may include. Additionally, humectants may also provide a base to serve as a base for construct a paste. Also, humectants may also help to retain moisture, thereby helping to prevent a toothpaste from drying out. Furthermore, humectants may help to prevent microbiological growth. Still further, humectants may add sweetness and/or provide other organoleptic effects. The humectant(s) may also help to give the composition a better feel to the mouth.

Humectants may also included in the present invention in concentration ranges of from about 5.0% to about 40.0% by weight. Further, humectants may be included in a concentration range of from about 15.0% to about 40.0% by weight.

The present invention may also include at least one abrasive. The abrasive may help to remove tobacco from surfaces, such as the teeth and gums, in the oral cavity after the nonionic surfactant(s), essential oil(s) and optionally other ingredients have at least partially dissolved, dispersed, solubilized, and/or detached the tobacco tar. The abrasives may be present in a concentration range of from about 5.0% to about 50.0% by weight. Alternatively, the present invention may include abrasives in a concentration range of from about 7.5% to about 35.0% by weight.

A variety of abrasives may be used in compositions according to the present invention. Examples of abrasives with a low abrasiveness include silica xerogels and/or silica precipitations. Examples of abrasives with a high abrasiveness include dicalcium phosphate, dicalcium phosphate dihydrate, alumina trihydrate, calcium pyrophosphate, calcium carbonate, insoluble sodium metaphosphate, and polymeric materials. Other examples of abrasives are provided by Oral Hygiene Products and Practice, Morton Pader, 1988, the entire contents of which is hereby incorporated by reference.

Compositions according to the present invention may include any one or more of the above or other abrasives. The amount and characteristics of the abrasive(s), such as abrasiveness, effects on dentin, abrasive effect on teeth, and hardness, included in a composition of the present invention may depend at least in part upon the amount of abrasiveness desired in the composition. The amount of tar on surface of a smoker's mouth may also effect the abrasiveness of the composition desired. In fact, specific formulations could be created to address various amounts of tar build up on teeth and other surfaces in smokers' mouths.

The present invention may also include at least one solvent. The solvent(s) may help to increase the activity of the essential oil(s) and nonionic surfactant(s) mixture. One example of a solvent that may be included in the present invention is ethanol. However, any pharmaceutically or orally acceptable solvent may be used.

The solvent(s) may be included in a range of from about 0.2% to about 7.5% by weight. Alternatively, the solvent(s) may be included in a range of from about 0.5% to about 5.5% by weight.

The present invention may also include a flavoring. The flavoring may be provided by one or more essential oils in addition to the methyl salicylate and/or other essential oil(s) discussed above as a tar solubilizer. Alternatively, the essential oil(s) and/or methyl salicylate discussed above may provide the flavoring. Any of the essential oils that may be utilized to solubilize tar may also be utilized as a flavoring.

Additionally, the present invention may include a preservative in concentration ranges of from about 0.01% to about 3.0% by weight. Alternatively, the present invention may include a preservative in a concentration range of from about 0.005% to about 0.01% by weight. Examples of such preservatives include benzoic acid and sodium benzoate, among others. However, any pharmaceutically or orally acceptable preservative may be used in compositions according to the present invention.

Further, the present invention may include a sweetener, such as sodium saccharin, in a concentration range of from about 0.01% to about 1.5% by weight. Alternatively, compositions according to the present invention may include a sweetener in a concentration range of from about 0.01% to about 0.7% by weight.

A color may also be added to the preparation of the present invention in a concentration range of from about 0.001% to about 0.5% by weight.

By including at least one nonionic surfactant and at least one essential oil, the present invention achieves it superior ability to dissolve, disperse, detach, solubilize, and/or otherwise remove tar from surfaces within the mouths of smokers, and especially the teeth and gums, particularly in conjunction with a toothbrush. Embodiments that include different types of surfactants may be even more effective at removing tar. For example, the present invention may include different surfactants that have different functionalities that act on the tar in different manners.

For instance, the present invention may include nonionic surfactants that act as tar solubilizers and anionic surfactants that act as detergents and detergent builders/sudsing aids. Anionic surfactants may help to suspend, dissolve, solubilize, detach and/or disperse tar particles as they are removed from the surfaces of the mouth. Anionic surfactants may include hydrophobic hydrocarbon side chains that help to solubilize the alkyl portions of the tar. In addition, methyl salicylate and/or other essential oil(s) may help to solubilize molecules in tobacco tar that include cyclic members.

No known prior art dental preparation includes the combination and amount of ingredients included in the present invention. It is the composition of the present invention that provides it with the unexpected ability to dissolve, detach, solubilize and/or disperse tobacco tar as effectively as it does in the amounts that it does.

As discussed above, the composition of the present invention may be provided in the form of gels or pastes by utilizing at least one material to increase the viscosity of the composition. Such viscosity increasing materials may include binders, thickening and/or gelling agents. Binders, thickeners, and gelling agents may help to provide a toothpaste firmness and/or extrudability, improve the mouthfeel, enhance the foamability, ensure phase stability, provide a smooth, shiny dentifrice, and/or make the dentifrice thixotropic.

Toothpastes typically include binders, thickeners and/or gelling agents of several different types. Such agents include, among others, silica aerogels, pyrogenic silica, silica precipitates, carboxymethyl cellulose, carboxyvinyl polymers, xanthan gum, and carrageenan. Other examples of binders, thickeners and/or gelling agents include inorganic gel-forming ingredients.

Examples of inorganic gel-forming ingredients used in toothpastes include silica precipitates, silica aerogels, pyrogenic silicas, colloidal magnesium aluminum silicate, and silicate clays. Another example of binders, thickeners and/or gelling agents includes modified cellulose products. Examples of modified cellulose products include carboxymethyl cellulose, hydroxyethyl cellulose, hydroxypropyl cellulose, hydroxymethyl carboxyethyl cellulose, hydroxymethyl carboxypropyl cellulose, methyl cellulose, ethyl cellulose, and sulfated cellulose.

A further example of binders, thickeners and/or gelling agents includes natural vegetable gums. Examples of natural vegetable gums include carrageenan, gum tragacanth, gum karaya, gum arabic, gum ghatti, gum acacia, locust bean gum, and sodium alginate. The gums could also have a bacterial origin. An example of a gum of bacterial origin is xanthan gum. Other natural origin binders, thickeners and/or gelling agents include, for example, agar, pectin, and gelatin.

Binders, thickeners and/or gelling agents may also include synthetic origin materials. Examples of synthetic materials include synthetic organic polymers. Examples of synthetic origin polymers include polyacrylate, and polyvinyl pyrrolidone.

Although any one or more binder, thickener, and/or gelling agent may be used, such as those discussed above, the most common binders, thickeners, and gelling agents include silicas, carrageenan, sodium carboxymethyl cellulose, xanthan gum, and carboxyvinyl polymers.

Binders, thickeners, and/or gelling agents may be included in the composition of the present invention in a concentration range of from about 0.5% to about 5.5% by weight. Alternatively, binders, thickeners, and/or gelling agents may be included in the composition of the present invention in a concentration range of from about 4.5% to about 5.5% by weight. On the other hand, the present invention may include an amount of binders, thickeners, and/or gelling agents sufficient to achieve a desired degree of toothpaste firmness, extrudability, mouthfeel, foamability, phase stability, smoothness, shininess, and/or thixotropicness.

The composition of the present invention may also include other ingredients for a variety of other purposes. For example, the present invention may include at least one fluoride containing material. The fluoride containing material may help to prevent cavities or dental caries.

Fluoride may be in an amount sufficient to help prevent cavities. Examples of the concentration range for fluoride in the composition of the present invention include from about 0.15% to about 0.50% by weight. Alternatively, the present invention may include fluoride in a concentration range of from about 0.25% to about 0.45% by weight.

In addition to the above ingredients, compositions of the present invention may also include water. The amount of water included in the composition may be enough to bring the total amount of all ingredients to 100% by weight.

The following example of a preferred embodiment is only illustrative. All amounts and proportions referred to here and in the claims are by weight unless otherwise indicated.

EXAMPLE 1

| Ingredient | Percent by weight |
| --- | --- |
| Abrasives | |
| Silica xerogel | 14.00 |
| Silica aerogel | 7.00 |
| Sodium carboxymethylcellulose | 1.00 |
| Essential oil | |
| Methyl salicylate | 0.20 |
| Nonionic surfactant | |
| PEG 40 hydrogenated castor oil | 2.50 |
| Sweetener | |
| Saccharin | 0.20 |
| Sorbitol solution (70%) | 69.50 |
| Coloring | |
| Dye solution (red) | 0.50 |
| Flavor | 2.00 |
| Anionic surfactant | |
| Sodium lauryl sulfate | 1.50 |
| Humectant | |
| Glycerin | 1.50 |
| Germicide | 0.10 |
| Total | 100.00 |

The exemplified formulation represents a satisfactory, pleasing, acceptable and effective deposit removing toothpaste having a satisfactory storage ability with respect to color, appearance, taste, and the like.

Generally, the composition may be prepared by adding the ingredients in the following two step sequence. First, all powdered components of the toothpaste, such as abrasives, gelling agents, thickening agents, therapeutic agents, sweeteners, whiteners, and colors, are blended together. This blending may help to avoid aggregation of the gelling agent(s). Next, all liquid ingredients, such as aqueous solutions, humectants, water, non-ionic surfactants, and flavoring, may be blended with the powdered ingredients. The blending of the liquid and powdered ingredients may be carried out in a heavy duty mixer. Following complete swelling of the gelling agent, a homogeneous paste may be formed.

To demonstrate the superior effectiveness of the present invention as compared to known toothpastes regarding effectiveness at removing tobacco tar from substrates was performed, experiments were performed. In the experiments, tobacco tar was applied to dental grade porcelain squares using a paint brush. The tobacco tar was obtained from CAMEL non-filtered cigarettes. The tar was permitted to dry at room temperature for 7 days.

After drying on the porcelain, 2 commercially available toothpastes and a composition according to the above example of the present invention were applied to the tar to compare their relative abilities to remove the tar from the porcelain. In particular, CREST and TOPAL toothpastes were compared to the present invention. ORAL B soft toothbrushes were utilized in all cases. The toothpastes were turned into foam by diluting them with water and agitating them before application to the tar covered substrates.

The experiment showed the dentifrice according to the present invention to be more than 50% more effective at removing the tobacco tar from the tar covered porcelain squares than the other commercial toothpastes. The foam created from the dentifrice according to the present invention actually discolored and turned brown. The discoloration shows that the present invention dissolved, solubilzed, detached and/or dispersed the tobacco tar. On the other hand, the commercially available toothpastes only removed tar through physical abrasion and appeared to have no ability to dissolve, solubilize, detach and/or disperse the tobacco tar. This demonstrated difference between the present invention and the prior art illustrates an important feature of the present invention, that is, the unique capability of dissolving tobacco tar.

Preparations according to the present invention are also suitable for use on denture material. In addition to being useful for dissolving tar, the present invention will also rapidly dissolve, solubilize, detach and/or disperse, remove from the mouth, and/or mask food, food odors, oils, and other hydrophobic materials, among other things.

The present invention also includes methods for removing deposits on surfaces of teeth, dentures, dental plates, and gums and surfaces in the oral cavity. The method includes introducing into the oral cavity an oral preparation including at least one nonionic surfactant and at least one essential oil. The composition may include any of the ingredients described above in the combinations and amounts described above. According to the method, surfaces in the oral cavity are then brushed with a toothbrush. The method may also include rinsing the oral cavity, dentures, and/or denture plates with water or an oral rinse. An example of an oral rinse is provided by co-pending U.S. patent application Ser. No. 08/642,358, the entire disclosure of which is hereby incorporated by reference.

Furthermore, the present invention includes methods for removing deposits on surfaces in the oral cavity resulting from the introduction into the oral cavity tobacco or material created by the burning of tobacco. The method includes introducing into the oral cavity an oral preparation including at least one nonionic surfactant and at least one essential oil. The composition may include any of the ingredients described above in the combinations and amounts described above. According to the method, surfaces in the oral cavity are then brushed with a toothbrush.

The present disclosure shows and describes only preferred embodiments of the present invention. As aforementioned, those reading the disclosure should understand that the invention may be used in other combinations and environments and may be changed or modified within the scope of the inventive concept expressed herein.

I claim:

1. A toothpaste for removing tobacco tar deposits on surfaces in the oral cavity in conjunction with a toothbrush, said preparation comprising:

an abrasive, and the combination of
at least one nonionic surfactant in a concentration range of from about 1.0% to about 40.0% by weight; and
at least one essential oil in a concentration range of from about 0.2% to about 13.0% by weight,
wherein the combination is effective to remove the tobacco tar deposits.

2. The toothpaste according to claim 1, wherein said at least one nonionic surfactant is included in a concentration range of from about 6.5% to about 40.0% by weight.

3. The toothpaste according to claim 1, wherein said at least one essential oil is methyl salicylate and is included in a concentration range of from about 0.2% to about 13.0% by weight.

4. The toothpaste according to claim 1, wherein said at least one essential oil is included in a concentration range of from about 2.0% to about 13.0% by weight.

5. The toothpaste according to claim 1, containing the abrasive in a concentration range of from about 5.0% to about 50.0% by weight, and further comprising at least one member of the group consisting of:

at least one anionic surfactant in a concentration range of from about 0.1% to about 3.5% by weight; and;
ethanol in a concentration range of from about 0.2% to about 7.5% by weight.

6. The toothpaste according to claim 5, wherein said anionic surfactant is selected from the group consisting of sodium lauryl sulfate and sodium ether lauryl sulfate.

7. The toothpaste according to claim 1, containing the abrasive in a concentration range of from about 7.5% to about 35.0% by weight, and further comprising at least one member of the group consisting of:

at least one anionic surfactant in a concentration range of from about 0.3% to about 2.5% by weight, and
ethanol in a concentration range of from about 0.5% to about 5.5% by weight.

8. The toothpaste according to claim 1, further comprising at least one member of the group consisting of:

at least one humectant in a concentration range of from about 5.0% to about 40.0% by weight,
at least one preservative in a concentration range of from about 0.005% to about 3.0% by weight,
at least one sweetener in a concentration range of from about 0.01% to about 1.5% by weight,
at least one fluoride-containing compound in a concentration range of from about 0.15% to about 0.50% by weight,
at least one coloring agent in a concentration range of from about 0.001% to about 0.5% by weight,
water in a concentration range of about an amount sufficient to bring the preparation to 100%, and at least one material for increasing the viscosity of said preparation in a concentration range of from about 0.5% to about 5.5% by weight.

9. The toothpaste according to claim 8, wherein said humectant includes at least one selected from the group consisting of glycerin and sorbitol.

10. The toothpaste according to claim 8, wherein said preservative includes at least one member selected from the group consisting of benzoic acid and sodium benzoate.

11. The toothpaste according to claim 8, wherein said sweetener is saccharine.

12. The toothpaste according to claim 1, further comprising at least one member of the group consisting of:

at least one humectant in a concentration range of from about 15.0% to about 40.0% by weight,
at least one preservative in a concentration range of from about 0.005% to about 0.01% by weight,
at least one sweetener in a concentration range of from about 0.01% to about 0.7% by weight,
at least one fluoride-containing compound in a concentration range of from about 0.25% to about 0.45% by weight,
at least one coloring agent in a concentration range of from about 0.001% to about 0.5% by weight,
at least one vehicle in a concentration range of about an amount sufficient to bring the preparation to 100%, and
at least one material for increasing the viscosity of said preparation in a concentration range of from about 4.5% to about 5.5% by weight.

13. The toothpaste according to claim 12, wherein said at least one vehicle is water.

14. The toothpaste according to claim 12, wherein said at least one viscosity increasing material is a thickener.

15. The toothpaste according to claim 1, wherein said at least one essential oil is a cyclic aromatic essential oil.

16. The toothpaste according to claim 1, wherein said nonionic surfactant is selected from the group consisting of glycerol-polyethylene glycol oxystearate, polyoxyethylene esters or sorbitol laurate esters, polyoxyethylene sorbitan monolaurate, polyoxyethylene sorbitan monoisostearate, polyoxyethylene sorbitan monostearate, polyoxyethylene sorbitan monooleate, polyoxyethylene laurate esters, sorbitol laurate esters including polysorbates, and block polymers of polyoxyethylene and polyoxypylene.

17. The toothpaste according to claim 1, wherein said at least one essential oil includes at least one member selected from the group consisting of methyl salicylate, anise, anethole, bergamot, camphor, cinnaminic anhydrides, clove, eucalyptol, peppermint, spearmint and thyme.

18. The toothpaste according to claim 1, wherein said at least one essential oil is methyl salicylate and is included in a concentration range of from about 0.5% to about 13.0% by weight.

19. A method for removing tobacco tar deposits on surfaces of teeth, dentures, dental plates, and gums and surfaces in the oral cavity, said method comprising the steps of:

introducing into the oral cavity a toothpaste containing an abrasive and the combination of at least one nonionic surfactant in a concentration range of from about 1.0% to about 40.0% by weight and at least one essential oil in a concentration range of from about 0.2% to about 13.0% by weight wherein the combination is effective to remove the tobacco tar deposits; and brushing surfaces in the oral cavity with a toothbrush.

20. A method for removing tobacco tar deposits on surfaces in the oral cavity resulting from the introduction into the oral cavity tobacco or material created by the burning of tobacco, said method comprising the steps of:

introducing into the oral cavity a toothpaste containing an abrasive and the combination of at least one nonionic surfactant in a concentration range of from about 1.0% to about 40.0% by weight and at least one essential oil in a concentration range of from about 0.2% to about 13.0% by weight wherein the combination is effective to remove the tobacco tar deposits; and brushing surfaces in the oral cavity with a toothbrush.

* * * * *